United States Patent [19]
Meghji

[11] Patent Number: 5,536,900
[45] Date of Patent: Jul. 16, 1996

[54] INBRED CORN LINE

[75] Inventor: Moez R. Meghji, Bloomington, Ill.

[73] Assignee: Ciba-Geigy Corporation, Tarrytown, N.Y.

[21] Appl. No.: 185,736

[22] Filed: Jan. 24, 1994

Related U.S. Application Data

[63] Continuation of Ser. No. 808,395, Dec. 16, 1991, abandoned.

[51] Int. Cl.$^6$ .............................. A01H 1/02; A01H 5/00; A01H 5/10
[52] U.S. Cl. ................ 800/200; 800/250; 800/DIG. 56; 47/58; 47/DIG. 1
[58] Field of Search ................................. 800/200, 250, 800/DIG. 56, 205, 235; 47/58.03, 58.05, DIG. 1, 58.01, 58

[56] References Cited

U.S. PATENT DOCUMENTS

| | | | |
|---|---|---|---|
| 4,806,652 | 2/1989 | Puskaric | 800/200 |
| 4,812,600 | 3/1989 | Jensen et al. | 800/200 |
| 5,097,094 | 3/1992 | Martin et al. | 800/200 |

OTHER PUBLICATIONS

Meghji et al. 1984 Crop Science 24:545–549.
Wych. 1988 In. Corn and Corn Improvement Sprague et al., eds. Ch. 9:565–607.

Bradley et al. J. Prod. Agric., vol. 1 (1988) pp. 34–38.
Phillips et al. (1988) Corn & Corn Improvement, Agronomy Monograph #18, 3rd ed, pp. 345–387.
Hallauer et al., Corn & Corn Improvement, Agromony Monograph #18, 3rd ed. (1988) pp. 463–564.
Hallauer et al., Quantitative Genetics in Maize Breeding Ames, Iowa, Iowa St. Univ. Press, 1981. pp. 123–126.
R. Forsberg et al., Chapter 4 in Hybridizatin in Crop Plants Madison, Wi, Amer. Soc. of Agronomy & Crop Science of America, 1980, pp. 65–81.
H. Wright, Ch. 8 of Hybridization in Crop Plants, pp. 161–176.
Allard. 1960, In Principles of Plant Breeding p. 68 John Wiley & Sons, Inc. N.Y., N.Y.

Primary Examiner—Erich E. Veitenheimer
Attorney, Agent, or Firm—Edward McC. Roberts

[57] ABSTRACT

According to the invention, there is provided an inbred corn line, designated CG00653. This invention thus relates to the plants and seeds of inbred corn line CG00653 and to methods for producing a corn plant produced by crossing the inbred line CG00653 with itself or with another corn line. This invention further relates to hybrid corn seeds and plants produced by crossing the inbred line CG00653 with another corn line.

5 Claims, No Drawings

12# INBRED CORN LINE

This application is a continuation, of application Ser. No. 07/808,395, filed Dec. 16, 1991, now abandoned.

FIELD OF THE INVENTION

This invention is in the field of hybrid corn (Zea mays L.) plant breeding, specifically relating to an inbred corn line designated CG00653.

BACKGROUND OF THE INVENTION

Of all the crops produced by U.S. farmers, corn is the crop that has the most economic value. Corn is utilized as livestock feed, as a basis for human consumption, as raw material for industry and as raw material for the production of ethanol. The primary use of farmer produced field corn is for livestock feed. This includes feed for hogs, beef cattle, dairy cows and poultry.

Human consumption of corn includes direct consumption of sweet corn and as snacks after extruder cooking, ground corn eaten as grits, corn meal and corn flour. Corn oil is also used as a high grade cooking oil, salad oil or in margarine. Corn is used in the production of some starches and syrups. Another important use is in the production of sweeteners used in soft drinks.

The wet-milling and dry-milling processes also produce corn starch and corn flour that have applications in industry. Some of these uses include building materials, the paper industry, textiles and starches.

The seed of inbred corn line CG00653, the plant produced by the inbred seed, the hybrid corn plant produced from the crossing of the inbred, hybrid seed, and various parts of the inbred and hybrid corn plant can be utilized for human food, livestock feed, and as a raw material in the industry.

The major reasons for the economic importance of corn and the large acreages planted to the crop are the hybridization of the corn plant and the continued improvement, by researchers, of the genetic stock that is used to produce the seed gown by farmers. This process has been on-going since its beginning in the early pan of the century. The average bushel per acre yield for the American farmer has gone from around 30 in the middle of the 1930's (before hybrids became dominant) to the present average of close to 120. While not all of this four-fold increase can be attributed to genetic improvement (availability of relatively cheap nitrogen and improvements in farming practices are two other components), a good share of it can.

Corn is easily hybridized because of the physical distance between the tassel (male pan) and the ear (female pan). The method of hybridization first involves the development of inbred lines. Inbred corn lines are considered to be homozygous, or, in essence, genetically the same from generation to generation. They are produced by taking the pollen from one plant and putting it only on the ear of that same plant. The resulting seed is gown, selections for uniformity and improved agonomic characteristics are made and the process is repeated until the seeds from the ears of the plants produce homozygous plants and the line is pure. A hybrid is then produced by crossing one inbred with another, genetically different, inbred. The crossing consists of taking the pollen from one inbred and putting it on the ear of the other inbred.

The seed from the crossing of two inbred lines is a first generation hybrid and is called an $F_1$. The $F_1$ of commercially viable hybrids have better yields, and other important characteristics, than either of the parents. This process is called hybrid vigor or heterosis. In succeeding generations ($F_2$, $F_3$, etc.) this heterosis is markedly reduced, making it economically justifiable for the farmer to go back to the seed company and obtain $F_1$ seed each year. As a result, the hybrid corn seed industry benefits both farmers and producers of hybrid corn seed.

The invention of new inbred lines and of new hybrids is extremely important to the companies in the hybrid seed corn industry that have investments in research. Much effort is given to the research and development of these inbreds and hybrids. The breeding and selection of inbred lines to be used as both seed parents and/or pollen parents and which when crossed to other inbred lines produce $F_1$ hybrid seed, which when planted, will produce plants that have characteristics that a farmer desires is a highly specialized skill. It involves many years of inbreeding, skilled selection, correct statistical testing, and decision making.

SUMMARY OF THE INVENTION

According to the invention, there is provided a novel inbred corn line, designated CG00653. This invention thus relates to the seeds of inbred corn line CG00653, to the plants of inbred corn line CG00653 and to methods for producing a corn plant produced by crossing the inbred line CG00653 with itself or another corn line. This invention further relates to hybrid corn seeds and plants produced by crossing the inbred line CG00653 with another corn line.

DEFINITIONS

This section will outline the definitions of terms used herein.

Yield (Bushels/Acre). The yield in bushels/acre is the actual yield of the grain at harvest adjusted to 15.5% moisture.

Percent Moisture. The moisture is the actual percentage moisture of the grain at harvest adjusted for test-weight.

Percent Erect. The percent erect is the percentage of plants that are still erect or standing at harvest.

Harvest Roots. Harvest roots is a visual rating. It is based on the number of plants that are root-lodged, i.e.; leaning from the vertical axis at an approximate 30° angle or greater. The ratings range from 1 to 9. A rating of 1 equals no plants root-lodged and a rating of 9 equals all plants root-lodged.

Percent Dropped Ears. The percent dropped ears is the percentage of plants that dropped (lost) their ears before harvest.

Percent Barren Plants. The percent barren plants is the percentage of plants that were barren (lacking ears).

Intactness. Intactness is a visual rating. It is based on the percentage of leaf and stalk matter remaining above the top ear at harvest. The ratings range from 1 to 9. A rating of 1 equals all matter remaining (intact) and a rating of 9 equals all matter gone or the stalk broken over just above the ear.

Percent Green. The percent green is the percentage of the total ear, leaf and stalk matter still green at the time of data collection, approximately physiological maturity.

Standard Index. Standard index gives a single measure of a hybrid's worth based on information for six traits. A corn breeder may utilize his or her own set of traits for the selection index.

DETAILED DESCRIPTION OF THE INVENTION

Inbred corn line CG00653 is a yellow dent corn with superior characteristics and provides an excellent parental line in crosses for producing first generation (F₁) hybrid corn. Inbred corn line CG00653 was selected for uniformity and agronomic traits from the proprietary Ciba-Geigy Seed Division (CGSD) source population D023N03. D023N03 is a recombination of lines out of Cycle 7 of the Iowa SSS population. In addition, six proprietary CGSD inbreds, 0464B, 5Y004B, CG00537, CG00545, CG00570 and ROC8201-9, were included in D023N03. Lines used to make up the population were intennated twice before selfing. $F_3$ ear-rows were evaluated and selected at the Rochelle, Ill. research station and the Bloomington, Ill. entomology support station. Selfing and selection continued to the $F_7$ generation at the Rochelle station and the Boynton Beach, Fla. winter nursery station. The inbred was evaluated further as a line and in numerous crosses by the Rochelle station and other research stations across the central corn belt. Thus the line was evaluated for general and specific combining ability. One particular cross showed outstanding performance in research testing across several research stations and was tested extensively over seven years of testing.

The inbred is adapted to the central corn belt and can be used advantageously in producing hybrids that are from approximately 100 day relative maturity to 110 day relative maturity based on the Minnesota Relative Maturity Rating System for harvest moisture of the grain. The inbred is an acceptable female parent for use in commercial hybrid seed corn production. The inbred could also be used as a male parent in the production of commercial hybrids. The inbred flowers earlier than the public inbred B73 and produces a better distribution of sized seed.

The inbred has shown relative uniformity and stability for all traits as described in the following variety description information. It has been self-pollinated and ear-rowed a sufficient number of generations with careful attention paid to uniformity of plant type to insure relative homozygosity and phenotypic stability. The line has been increased by hand pollination and in isolated fields with continued observations for uniformity. No particular variant traits have been observed or are expected in CG00653.

Inbred corn line CG00653 can be compared to the public inbred B73. The characteristics of CG00653 versus B73 are summarized below (based primarily on data collected at Bloomington, Ill.):

|  | CG000653 | B73 |
| --- | --- | --- |
| MATURITY | | |
| Days from emergence to 50% of plants in silk | 64 | 68 |
| Heat units from emergence to 50% of plants in silk | 1360 | 1436 |
| Days from emergence to 50% of plants shedding pollen | 66 | 68 |
| Heat units from emergence to 50% of plants shedding pollen | 1399 | 1440 |
| PLANT CHARACTERISTICS | | |
| Plant height to tassel tip (cm) | 195 | 238 |
| Ear height to top ear node (cm) | 52 | 104 |
| Length of top ear internode (cm) | 13 | 15 |
| Ears per stalk | Slight two-ear tendency | Single |
| Number of tillers | None | None |
| Anthocyanin in brace roots | Absent | Present |
| Cytoplasm type | Normal | Normal |
| LEAF | | |
| Color | Dark green | Dark green |
| Angle from stalk (degrees) | <30 | <30 |
| Sheath pubescence | Medium | Medium |
| Marginal waves | Many | Few |
| Longitudinal creases | Few | Few |
| Width of ear node leaf at widest point (cm) | 8 | 9 |
| Length of ear node leaf (cm) | 66 | 84 |
| Number of leaves above the ear node | 6 | 5 |
| TASSEL | | |
| Number of lateral branches | 10 | 9 |
| Branch angle from central spike (degrees) | 45 | 15 |
| Peduncle length (cm) | 8 | 9 |
| Pollen shed | Light | Medium |
| Anther color | Green | Purple |
| Glume color | Green | Green |
| Glume bars | Absent | Absent |
| EAR (Husked Ear Data at 12.5% Kernel Moisture) | | |
| Length (cm) | 11 | 12 |
| Mid-point diameter (mm) | 35 | 46 |
| Weight (gm) | 62 | 83 |
| Kernel rows | 14, somewhat indistinct, straight | 16, distinct, straight |

|  | CG000653 | B73 |
| --- | --- | --- |
| Silk color | Green | Green |
| Husk color (fresh) | Dark green | Light green |
| Husk color (dry) | Buff | Buff |
| Husk extension | Medium (barely covering ear) | Medium (barely covering ear) |
| Husk leaf | Medium (8–15 cm) | Short (<8 cm) |
| Shank Length (cm) | 9 | 9 |
| Shank (no. of internodes) | 4 | 4 |
| Position of shank (dry husks) | Upright | Upright |
| Taper | Average | Slight |
| KERNEL (at 12.5% kernel moisture) | | |
| Size (kernels taken from ear midpoint) | 9 mm long, 6 mm wide, 4 mm thick | 11 mm long, 6 mm wide, 4 mm thick |
| Shape grade (% rounds) | 13 | 17 |
| Pericarp color | Colorless | Colorless |
| Aleurone color | Homozygous, white | Homozygous, white |
| Endosperm color | Yellow | Yellow |
| Endosperm type | Normal starch | Normal starch |
| Gram weight/100 seeds (unsized sample) | 20 | 17 |
| Test weight (pounds) | 61 | 55 |
| COB | | |
| Diameter at midpoint (mm) | 22 | 32 |
| Strength | Weak | Weak |
| Color | Red | Red |

Disease reaction information for CG00653 are given below:

| Anthracnose leaf blight | Moderately resistant |
| --- | --- |
| Common rust | Moderately resistant |
| Common smut | Resistant |
| Maize dwarf mosaic A | Moderately susceptible |
| Maize dwarf mosaic B | Moderately susceptible |
| Wheat streak mosaic | Resistant |

Heat units calculations are derived by using the following formula: Heat Units equals [Daily Maximum Temperature (<86° F.) plus Daily Minimum Temperature (>50° F.)] divided by 2 minus 50° F.

This invention is also directed to methods for producing a corn plant by crossing a first parent corn plant with a second parent corn plant wherein the first or second corn plant is the inbred corn plant from the line CG00653. Further both first and second parent corn plants may be from the inbred line CG00653. Thus, any methods using the inbred corn line CG00653 are part of the invention: backcrosses, hybrid breeding, and crosses to populations. Any plants produced using inbred corn line CG00653 as a parent are within the scope of this invention. Advantageously, the inbred corn line CG00653 is used in crosses with other corn varieties to produce first generation ($F_1$) corn hybrid seed and plants with superior characteristics.

As used herein, the term "plant" includes plant cells, plant protoplasts, plant cell of tissue culture from which corn plants can be regenerated, plant calli, plant clumps, and plant cells that are intact in plants or pans of plants such as pollen, flowers, kernels, ears, cobs, leaves, husks, stalks, and the like. Thus another aspect of this invention is to provide for cells which upon growth and differentiation produce the inbred line CG00653.

Electrophoresis results for CG00653 and the public inbreds B73 and B68 am shown in Table 1 below:

TABLE 1

| | Electrophoresis results for CG00653, B73 and B68 | | |
| --- | --- | --- | --- |
| | | Alleles Present | |
| Locus | CG00653 | B73 | B68 |
| Acp1 | 2 | 2 | 3 |
| Adh1 | 4 | 4 | 4 |
| Cat3 | 9 | 9 | 9 |
| Got1 | 4 | 4 | 4 |
| Got2 | 4 | 4 | 4 |
| Got3 | 4 | 4 | 4 |
| Idh1 | 4 | 4 | 4 |
| Idh2 | 6 | 4 | 6 |
| Mdh1 | 6 | 6 | 6 |
| Mdh2 | 6 | 3.5 | 6 |
| Mdh3 | 16 | 16 | 16 |
| Mdh4 | 12 | 12 | 12 |
| Mdh5 | 12 | 12 | 12 |
| Mmm | — | — | — |
| Pgm1 | 9 | 9 | 9 |
| Pgm2 | 4 | 4 | 4 |
| Pdg1 | 2,3.8 | 3.8 | 2 |
| Pdg2 | 5 | 5 | 5 |
| Phi1 | 4 | 4 | 5 |
| No. plants | 36 | 24 | 24 |

The data in Table 2 shows the relative hybrid performance of corn inbred line CG00653 crossed to CGSD corn inbred line CG00567, hereinafter CG00653×CG00567, compared to CGSD corn inbred line CG00502 crossed to CGSD corn inbred line CG00567, hereinafter CG00502×CG00567. Corn hybrid CG00502×CG00567 is a proprietary CGSD hybrid currently being sold in the central United States. The data was averaged across all locations and replications and would include experiments grown by seventeen CGSD corn research programs in 1989 and 1990.

TABLE 2

Corn hybrid CG00653 × CG00567 compared to CG00502 × CG00567

| | HYBRID | | | | |
|---|---|---|---|---|---|
| | Yield (BU/A) | Percent Moisture | Percent Erect | Harvest Roots | Percent Dropped Ears |
| | No. Locations | | | | |
| | 351 | 355 | 341 | 96 | 301 |
| CG00653 × CG00567 | 145 | 19.8 | 92.4 | 1.5 | 0.45 |
| CG00502 × CG00567 | 138 | 19.7 | 93.9 | 1.5 | 0.47 |
| Difference | 7 | 0.1 | 1.5 | 0 | 0.02 |

| | HYBRID | | | |
|---|---|---|---|---|
| | Percent Barren Plants | Intactness | Percent Green | Standard Index |
| | No. Locations | | | |
| | 12 | 313 | 76 | 428 |
| CG00653 × CG00567 | 7.9 | 5.1 | 43.3 | 197 |
| CG00502 × CG00567 | 10.4 | 5.5 | 34.8 | 192 |
| Difference | 2.5 | 0.4 | 8.5 | 5 |

The data show that both CG00653 and CG00502 make hybrids of similar maturity (percent moisture). The results show CG00653 has an advantage over CG00502 for percent barren plants, intactness and percent green. In this and other hybrid combinations, CG00653 has shown outstanding yield performance relative to other commercially sold hybrids of similar maturity At least 2,500 inbred seeds of CG00653 have been placed on deposit at the American Type Culture Collection (ATCC), Rockville, Md., 20852, under deposit accession number 75161 on Nov. 27, 1991.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An inbred corn line designated CG00653, the seeds of which have been deposited as ATCC Accession No. 75161.

2. Plants of the inbred corn line designated CG00653 of claim 1.

3. An inbred corn plant with the phenotypic, physiological and morphologic characteristics of the inbred corn line designated CG00653, where in the seeds of CG00653 have been deposited as ATCC Accession No. 75161.

4. A method of maintaining an inbred corn line comprising crossing a first parent corn plant with a second parent corn plant, wherein both of said first and second parent corn plants are inbred parent corn plants having the designation CG00653, wherein the seeds of CG00653 have been deposited as ATCC Accession No. 75161.

5. Seed of the inbred corn line designated CG00653 of claim 1.

* * * * *